(12) United States Patent
Kaiser et al.

(10) Patent No.: US 11,458,333 B2
(45) Date of Patent: Oct. 4, 2022

(54) SURFACE-GUIDED X-RAY REGISTRATION

(71) Applicant: Brainlab AG, Munich (DE)

(72) Inventors: Hagen Kaiser, Icking (DE); Jochen Veigel, Rosenheim (DE); Ivana Ivanovska, Aschheim (DE); Pablo Aponte, Haar (DE)

(73) Assignee: Brainlab AG, Munich (DE)

( * ) Notice: Subject to any disclaimer, the term of this patent is extended or adjusted under 35 U.S.C. 154(b) by 824 days.

(21) Appl. No.: 16/333,905

(22) PCT Filed: Jun. 18, 2018

(86) PCT No.: PCT/EP2018/066107
§ 371 (c)(1),
(2) Date: Mar. 15, 2019

(87) PCT Pub. No.: WO2018/234237
PCT Pub. Date: Dec. 27, 2018

(65) Prior Publication Data
US 2019/0201716 A1 Jul. 4, 2019

Related U.S. Application Data

(63) Continuation-in-part of application No. PCT/EP2017/065424, filed on Jun. 22, 2017.

(51) Int. Cl.
*A61N 5/10* (2006.01)
*G06T 7/73* (2017.01)
(Continued)

(52) U.S. Cl.
CPC ........... *A61N 5/1039* (2013.01); *A61N 5/103* (2013.01); *A61N 5/1031* (2013.01);
(Continued)

(58) Field of Classification Search
CPC .... A61N 5/103–107; A61N 5/10–1084; A61N 2005/1085–1098
See application file for complete search history.

(56) References Cited

U.S. PATENT DOCUMENTS

| 5,951,475 A | 9/1999 | Gueziec et al. |
| 6,405,072 B1 | 6/2002 | Cosman |

(Continued)

FOREIGN PATENT DOCUMENTS

| WO | WO2014066906 A1 | 5/2014 |
| WO | WO2018234237 A1 | 12/2018 |

OTHER PUBLICATIONS

Krengli, Marco et al., Reproducibility of Patient Setup by Surface Image Registration System in Conformal Radiotherapy of Prostate Cancer, Radiation Oncology. 4:9, Feb. 22, 2009.
(Continued)

*Primary Examiner* — Thaddeus B Cox
(74) *Attorney, Agent, or Firm* — Middleton Reutlinger (57) ABSTRACT

Disclosed is a computer-implemented method for determining the pose of an anatomical body part of a patient's body for planning radiation treatment, a corresponding computer program, a non-transitory program storage medium storing such a program and a computer for executing the program, as well as a system for determining the pose of an anatomical body part of a patient's body for planning radiation treatment, the system comprising an electronic data storage device and acquire surface tracking data the aforementioned computer.

13 Claims, 4 Drawing Sheets

(51) Int. Cl.
  *G06K 9/62*    (2022.01)
  *G06T 7/00*    (2017.01)
  *G06V 10/143*  (2022.01)
  *G06V 10/75*   (2022.01)
  *G06T 7/32*    (2017.01)
  *G06T 7/70*    (2017.01)
  *A61B 34/20*   (2016.01)
  *A61B 90/00*   (2016.01)
  *G06V 10/62*   (2022.01)

(52) U.S. Cl.
  CPC ......... *A61N 5/1067* (2013.01); *G06K 9/6215* (2013.01); *G06T 7/0012* (2013.01); *G06T 7/32* (2017.01); *G06T 7/70* (2017.01); *G06T 7/75* (2017.01); *G06V 10/143* (2022.01); *G06V 10/754* (2022.01); *A61B 2034/2055* (2016.02); *A61B 2034/2065* (2016.02); *A61B 2090/364* (2016.02); *A61N 5/107* (2013.01); *A61N 5/1064* (2013.01); *A61N 5/1069* (2013.01); *A61N 2005/105* (2013.01); *A61N 2005/1059* (2013.01); *A61N 2005/1061* (2013.01); *A61N 2005/1062* (2013.01); *G06T 2207/10028* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/20221* (2013.01); *G06T 2207/30004* (2013.01); *G06V 10/62* (2022.01); *G06V 2201/033* (2022.01)

(56) References Cited

U.S. PATENT DOCUMENTS

| | | |
|---|---|---|
| 2005/0096515 A1 | 5/2005 | Geng |
| 2008/0049014 A1 | 2/2008 | Haimerl et al. |
| 2016/0310761 A1* | 10/2016 | Li .................. G06K 9/6267 |
| 2017/0165501 A1* | 6/2017 | Rapaka ............ A61N 5/1031 |

OTHER PUBLICATIONS

BL, Lindl et al., TOPOS: A New Topometric Patient Positioning and Tracking System for Radiation Therapy Based on Structured White Light, Med Phys, Apr. 2013.

International Search Report and Written Opinion of PCT Application PCT/EP2018/066107, dated Sep. 21, 2018.

* cited by examiner

Fig. 4

SURFACE-GUIDED X-RAY REGISTRATION

The present invention relates to a computer-implemented method for determining the pose of an anatomical body part of a patient's body for planning radiation treatment, a corresponding computer program, a non-transitory program storage medium storing such a program and a computer for executing the program, as well as a system for determining the pose of an anatomical body part of a patient's body for planning radiation treatment, the system comprising an electronic data storage device and the aforementioned computer.

TECHNICAL BACKGROUND

The present invention relates specifically to determining the position of a patient relative to the isocentre of a linear accelerator based on x-rays in challenging conditions (i.e. monoscopic, rib-cage) using surface matching as auxiliary technique.

It is known to use mono or stereoscopic x-ray registration between bony anatomy or implanted markers in a CT (computed tomography) against DRRs (digitally rendered x-ray reconstructions) to determine the position of a patient relative to its CT image representation that has been placed virtually relative to the isocentre of the linear accelerator. Alternatively, positioning has been performed using x-ray imagers mounted on the linear accelerator co-registered against portal images.

The present invention is designed to provide an improved method for planning radiation treatment.

The present invention can be used in connection with a system for image-guided radiotherapy such as ExacTrac®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses determining whether the pose of a patient's body when placing him in a state ready for radiotherapy or radiosurgery is as desired. To this end, two-dimensional x-ray images (fluorographies) are acquired from patient and compared to DRRs rendered from a planning tomography (such as a CT or MR) to receive a measure of similarity between the pose described by an x-ray image and the DRR. Additionally, the surface of the patient's body is scanned e.g. with a laser scanning device to generate a dataset representing the current geometry and position of the surface which is then compared to a corresponding surface generated from the planning tomography to receive a measure of similarity between the poses described by the current surface geometry and position and the corresponding quantities generated from the planning tomography. The two measures of similarity are input into an optimizer to optimize the pose of the patient so that an optimal value of both measures of similarity is obtained in an iterative procedure. This allows to reach an optimal patient positioning.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented medical data processing method for determining the pose of an anatomical body part of a patient's body for planning radiation treatment (which may be for example at least one of radiotherapy or radiosurgery). The method comprises executing, on at least one processor of at least one computer (for example at least one computer being part of the navigation system), the following exemplary steps which are executed by the at least one processor.

In a (for example first) exemplary step, three-dimensional reference image data is acquired which describes a reference image (for example, a computed x-ray tomography—reference CT—or a magnetic resonance tomography—reference MRT) of both a reference pose of an internal anatomical reference structure of the anatomical body part and a reference pose of an anatomical reference surface of the anatomical body part. Within tis disclosure, the term "pose" means "position in six degrees of freedom", i.e. location and orientation (in combination).

In a (for example second) exemplary step, surface tracking data is acquired which describes a tracking image of a current pose of the anatomical reference surface of the anatomical body part. In one example, the internal anatomical reference structure comprises or consists of bony tissue (such as at least part of the rib cage), and wherein the anatomical reference surface is an external surface of the patient's body.

In a (for example third) exemplary step, a reference surface pose similarity measure is determined by comparing the reference pose of the anatomical reference surface and the current pose of the anatomical reference surface. For example, the reference surface pose similarity measure is or has been determined by determining an average deviation of surface points or a correspondence of topological equivalents or an image fusion, for example elastic image fusion, between the reference image and the tracking image. For example, the reference structure pose similarity measure is determined by determining a rigid image fusion between the reconstructed two-dimensional reference image and the current two-dimensional image.

In a (for example fourth) exemplary step, reconstructed image data which describes a reconstructed two-dimensional reference image (for example, a digitally reconstructed radiograph—DRR) of the internal anatomical reference structure is generated from the reference image data.

In a (for example fifth) exemplary step, current reference structure image data is acquired which describes a current two-dimensional image of a current pose of the internal anatomical reference structure.

In a (for example sixth) exemplary step, a reference structure pose similarity measure is determined by comparing the reference pose of the internal anatomical reference structure and the current pose of the internal anatomical reference structure.

In a (for example seventh) exemplary step, an optimized pose of the anatomical body part is determined which is associated with optimal values of the reference surface pose similarity measure and the reference structure pose similarity measure. In one example, the method according to the preceding claim, wherein the optimized pose is determined based on the reference surface pose similarity measure and the reference structure pose similarity measure.

For determining the optimized pose, the reference surface pose similarity measure and the reference surface pose similarity measure are in one example input into an optimization algorithm (such as the one described in Powell M. J., UOBYQA: unconstrained optimization by quadratic approximation. Cambridge: Department Applied Mathematics and Theoretical Physics, Cambridge University, December 2000 for simultaneously minimizing any dissimilarity between the reference pose of the internal anatomical reference structure and the current pose of the internal anatomical reference structure and any dissimilarity between the reference pose of the anatomical reference surface and the current pose of the anatomical reference surface.

In one example of the disclosed method, planning image data is acquired which describes a planned pose of the anatomical body part. The planning image data is for example a computed x-ray tomography—planning CT- or a magnetic resonance tomography—planning MRT. The planning image data and the reference image data may in one example be at least partly identical (for example, if at least part of the planning CT or planning MR is used as the reference CT or reference MRT). The optimized pose is compared to the planned pose. Determining the optimized pose in one example comprises changing (for example, virtually changing) the reference pose of the internal anatomical structure. The effect of such a procedure is that the quality of the optimized pose may be determined.

In examples, the disclosed method comprises at least one of the following steps:

a (for example, digital and/or electronic) control signal for controlling (for example, activating or de-activating, blocking or unblocking) emission of a radiation treatment beam by a radiation treatment apparatus is determined based on the result of the comparison; or a (for example, digital and/or electronic) control signal for controlling (e.g. physically changing and/or moving) the position of a patient support device (such as a couch) supporting the anatomical body part is determined based on the result of the comparison.

The reference image data has in one example been generated by applying an x-ray-based imaging modality such as radiography or computed x-ray tomography or cone beam computed x-ray tomography to the anatomical body part and the reconstructed two-dimensional reference image is a digitally reconstructed radiograph. In other example, the reference image data has been generated by applying a magnetic resonance imaging modality or ultrasound imaging modality to the anatomical body part.

In one example of the method, wherein surface tracking data has been generated by applying a structured light tracking modality or three-dimensional thermal tracking modality (or a combination of structured light and thermal tracking modality) or surface scan laser tracking modality or visible digital photography tracking modality or a time-of-flight tracking modality to the anatomical body part.

In one example, the current reference structure image data has been generated by applying an x-ray-based imaging modality such as stereoscopic or monoscopic radiography or cone beam computed x-ray tomography or a magnetic resonance imaging modality to the anatomical body part.

In one example, the reconstructed image data and the current reference structure image data describe images of the same or a comparable (such as an x-ray image and a computed x-ray tomography) imaging modality. In a different example, the reconstructed image data and the current reference structure image data describe images of different imaging modalities. The method then for example comprises a step of acquiring atlas data describing a multimodal atlas of the anatomical body part, wherein the reference structure pose similarity measure is determined based on the atlas data. For example, at least one of the reference structure image data and the reconstructed image data is transformed into a common imaging modality, for example the imaging modality of the other of the reference structure image data and the reconstructed image data, based on the atlas data, wherein the reference structure pose similarity data is determined based on the transformed at least one of the reference structure image data and the reconstructed image data.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to a system for determining a deviation between a planned and a current pose between an anatomical body part and a treatment beam source (for example, a radiation treatment system), the system comprising:

a) the at least one computer according to the preceding claim;

b) at least one electronic data storage device storing at least the reference image data and planning image data which describes a planned pose of the anatomical body part relative to the treatment beam source; and c) a medical imaging device (such as a stereoscopic and/or fluoroscopic x-ray device) for generating the current reference structure image data, d) an optical tracking device for generating the surface tracking data, wherein the medical imaging device and the optical tracking device are operably coupled to the at least one computer for transmitting a signal to the at least one computer corresponding to the current reference structure image data and the surface tracking data; and e) a radiation treatment apparatus comprising a treatment beam source and a patient support unit, wherein the at least one computer is operably coupled to the at least one electronic data storage device for acquiring, from the at least one data storage device, at least the reference image data and the planning image data, and for issuing a control signal to the radiation treatment apparatus for controlling at least one of the functionality of the treatment beam source or the position of the patient support unit on the basis of the result of comparing the planned pose with the optimized pose.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of radiotherapy or radiosurgery. More particularly, the invention does not involve or in particular comprise or encompass any surgical or therapeutic activity. The invention is instead directed as applicable to positioning a patient relative to the treatment device for example before any radiotherapy or radiosurgery ensues. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument).

For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface.

The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use.

The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data".

Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention relates to the field of controlling a treatment beam. The treatment beam treats body parts which are to be treated and which are referred to in the following as "treatment body parts". These body parts are for example parts of a patient's body, i.e. anatomical body parts.

Ionising radiation is an example of radiation emittable by the radiation treatment apparatus and is used for example for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation.

The tumour is then an example of an anatomical body part.

DESCRIPTION OF THE FIGURES

In the following, the invention is described with reference to the appended figures which give background explanations and represent specific embodiments of the invention. The scope of the invention is however not limited to the specific features disclosed in the context of the figures, wherein.

Figure 1:
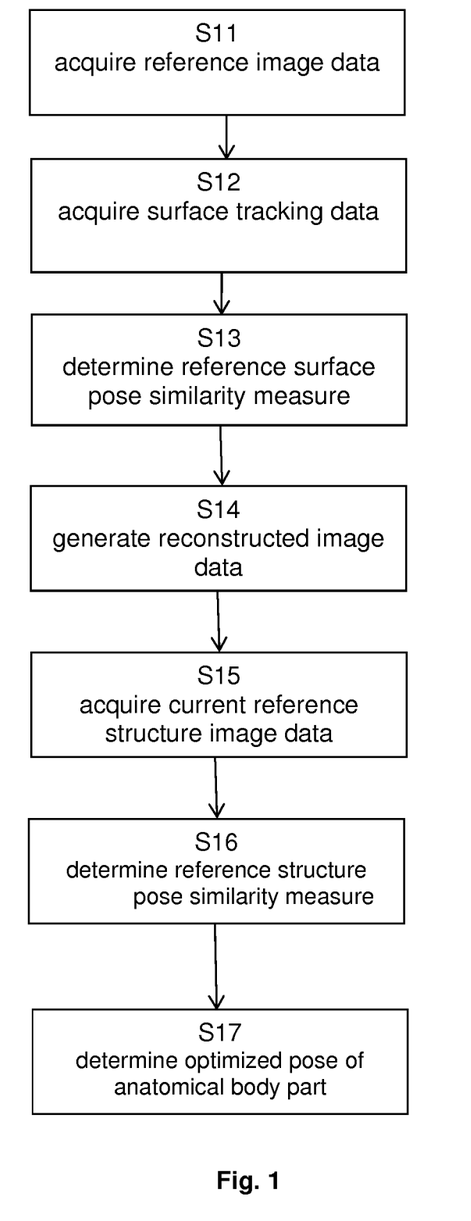
FIGS. 1 and 2 illustrate two examples of the method according to the first aspect.

FIG. 1 is a flow diagram illustrating the basic steps of the disclosed method in accordance with the first aspect, which in the illustrative example of FIG. 1 starts with a step S11 of acquiring the reference image data. In subsequent step S12, the surface tracking data is acquired, followed by step S13 which encompasses determining the reference surface pose similarity measure. Then, step S14 generates the reconstructed image data. Subsequent step S15 is directed to acquiring the current reference structure image data. Step S16 then continues with determining the reference structure pose similarity measure, followed by step S17 of determining the optimized pose of the anatomical body part. Steps S11 to S16 and/or the data outputted by those steps serve as input steps to step S17.

Figure 2:
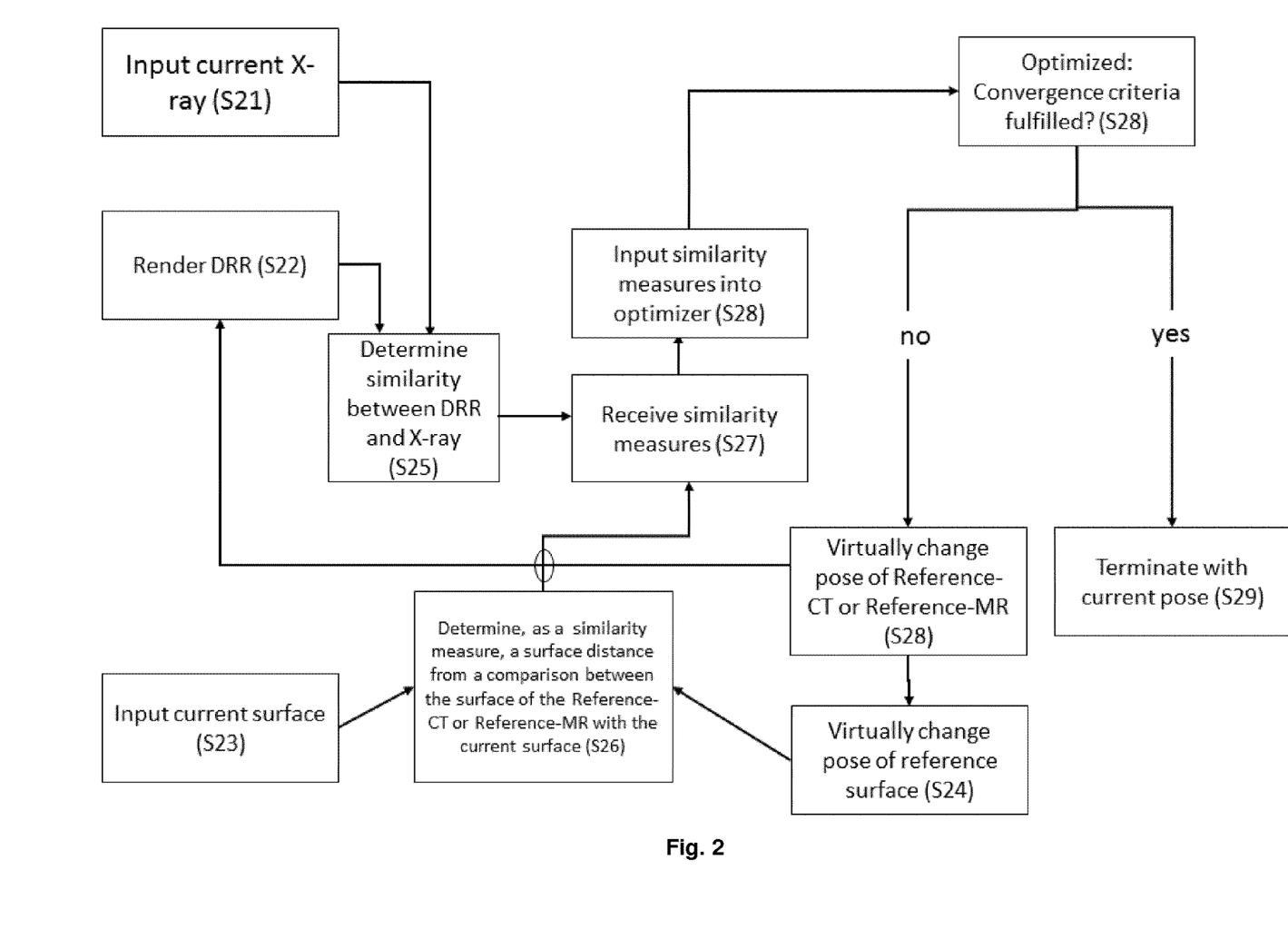

FIG. 2 illustrates a second example of the method according to the first aspect. The reference image data is input as a Reference-CT or Reference-MR, and a DRR is rendered from the Reference-CT or Reference-MR in step S22. A current two-dimensional x-ray image (fluoroscopy/radiography) taken with a flat panel array used as the medical imaging device of the system according to the fifth aspect is input in step S21. The similarity between the DRR and the current x-ray is determined in step S25, for example by executing a fusion algorithm on the two data sets. Furthermore, information about a current surface of the patient's body is input in step S23 as the surface tracking data, and a similarity measure is determined in step S26 between the current surface and a corresponding surface included in the Reference-CT or Reference-MR, respectively. The similarity measures representing the similarity between the DRR and the current x-ray output by step S25 and the similarity measure representing the similarity between the current surface and a corresponding surface included in the Reference-CT or Reference-MR output by step S26 are received in step S27. Subsequently, the similarity measures are input in step S28 into an optimizer, e.g. the optimizer described by Powell M. J., UOBYQA: unconstrained optimization by quadratic approximation. Cambridge: Department Applied Mathematics and Theoretical Physics, Cambridge University, December 2000. The method determines in step S28, whether a predetermined convergence criterion is fulfilled by the output of the optimizer. If this is the case, the method terminates with the current pose as the optimized pose in step S29. If the result of step S28 is that the convergence criterion is not fulfilled, the step continues with virtually changing the reference pose in step S28 and re-using this changed reference pose as an input for a further iteration of the method, starting with rendering the DRR from the virtually changed Reference-CT or Reference-MR in step S22. The virtually changed reference surface is additionally input via step S24 into step S26 for comparing the virtually changed reference surface to the current surface.

If monoscopic x-ray registration is required, the method performs the known 6 DoF (six degrees of freedom) x-ray registration algorithm using a single x-ray and a surface match simultaneously. The surface match is performed using a surface acquired by a 3D scanner (a CT scanner or MR scanner) at the time of determining the monoscopic x-ray registration and either a surface that has been recorded and saved directly after positioning the patient or the outer contour of the planning CT (reference-CT).

The 3D camera can be mounted in central position in front of the linear accelerator such that no gantry angle ever blocks the line of sight of the 3D scanner to the patient. This simultaneous surface/x-ray registration is achieved by calculating the error of the surface match given the current iterations pose yielded by the x-ray registration and adding that error to the x-ray registration. The same principle can be of course applied to stereoscopic imaging, where the error of the surface match is simultaneously minimized along with the error of the x-ray images.

Surface Guided x-Ray Registration

The function to minimize used by the optimizer is as follows:

$$\min_p(\varphi(x_{ref}(p), x_{curr}) + \alpha \cdot \phi(s_{ref}(p), s_{curr}))$$

$\varphi$ measures the similarity between $x_{ref}(p)$, a reference DRR, based on assumed pose p and current x-ray. $\alpha$ is a weighting factor, $\phi$ denotes the match quality between $s_{ref}(p)$, a reference surface warped to pose p, and a current surface snapshot taken by the 3D scanner. As can be seen in FIG. 2, a possible optimization i.e. (Powell, December 2000) algorithm varies the assumptions about the current position of the patient. Given these assumptions DRRs are rendered and compared with the current x-ray image(s) which result in an error. At the same time the surface match quality is computed given the current pose. Both results are added and presented to the optimizer. Poses p are varied until the summed error is minimal. The reference surface can be initialized taking a snapshot using the scanner or by using the outer contour of the planning CT.

Performing a simultaneous minimization of the surface match error and the x-ray match error should constrain the x-ray minimizations intermediate results in a small eta environment around the surface matches end result. This should preserve the pure x-ray registration from falling into local minima due to ambiguities. It thus is possible to calculate full 6 DoF shifts for monoscopic images.

Furthermore, repetitive structures can be resolved correctly as a convergence of the registration to the 'wrong' rib or 'wrong' vertebra would yield a severely bad result in the surface match.

Such an algorithm facilitates therefore a full 6 DoF monitoring which is independent of the gantry angle as well as a safe x-ray positioning on repetitive structures such as the rib cage and therefore solves the two most prominent problems of the x-ray registration principle used with known linear accelerators (LINACs).

6D Registration Using LINAC-Mounted kV Imaging System and a Surface Scanner

In one embodiment the principle of this invention could be used to improve the results of the kV imaging device that is mounted to the LINAC. To make sure the 3D camera has constant line of sight to the patient the 3D camera is mounted to the top of the gantry. Thus it has an orthogonal view on the patient in relation to the kV imaging system mounted to the sides if the LINAC (see Powell, December 2000).

6D Registration Using Ceiling Mounted (Stereoscopic) x-Ray and a Surface Scanner In another embodiment the principle could be used to improve a stereoscopic setup as it is used in known LINACs. A central mounting of the 3D scanner as it can be seen in Powell, December 2000, facilitates a line of sight of the 3D scanner to the patient independently of the gantries rotation. However, the line of sight of either the left or the right x-ray imager could be blocked.

Using the principle of the invention it can be made sure that at least one of the two x-ray imagers is available at the same time as the 3D scanner. Thus the surface guided x-ray registration can be used at all times.

Figure 3:
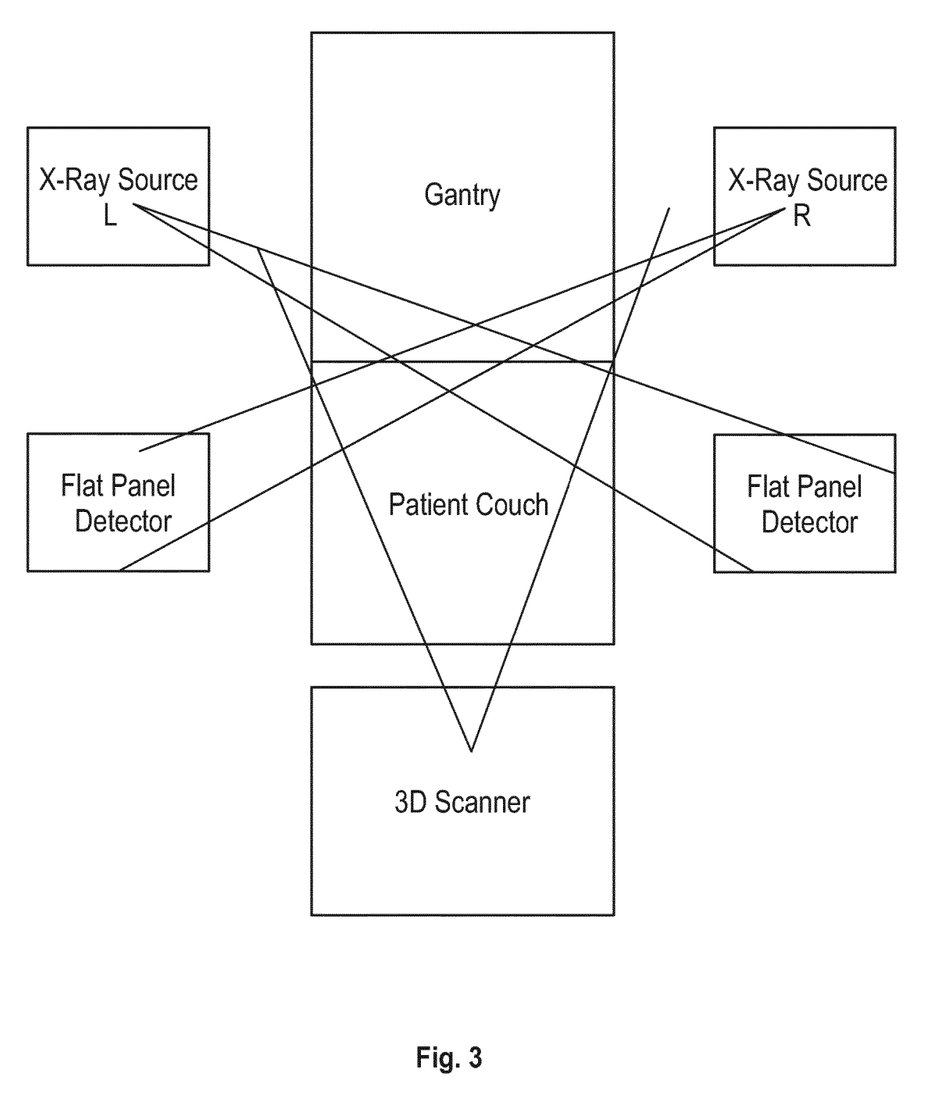
FIGS. 3 and 4 illustrate two views of the system according to the fifth aspect.

FIG. 3 shows a first example of the system according to the fifth aspect. A radiation treatment system comprises, as a stereoscopic medical imaging device, each a left (L) and right (R) x-ray source which images a patient placed on a patient couch via cross-wise corresponding flat panel detectors. Treatment radiation is emitted onto the patient from a linear accelerator located in the gantry which can rotate around the patient. Additionally, a 3D scanner (e.g. a laser scanner) for generating the information about the current surface/the surface tracking data is included in the system so that it can view the patient placed on the patient couch without its view of the patient being obstructed by the gantry.

Figure 4:
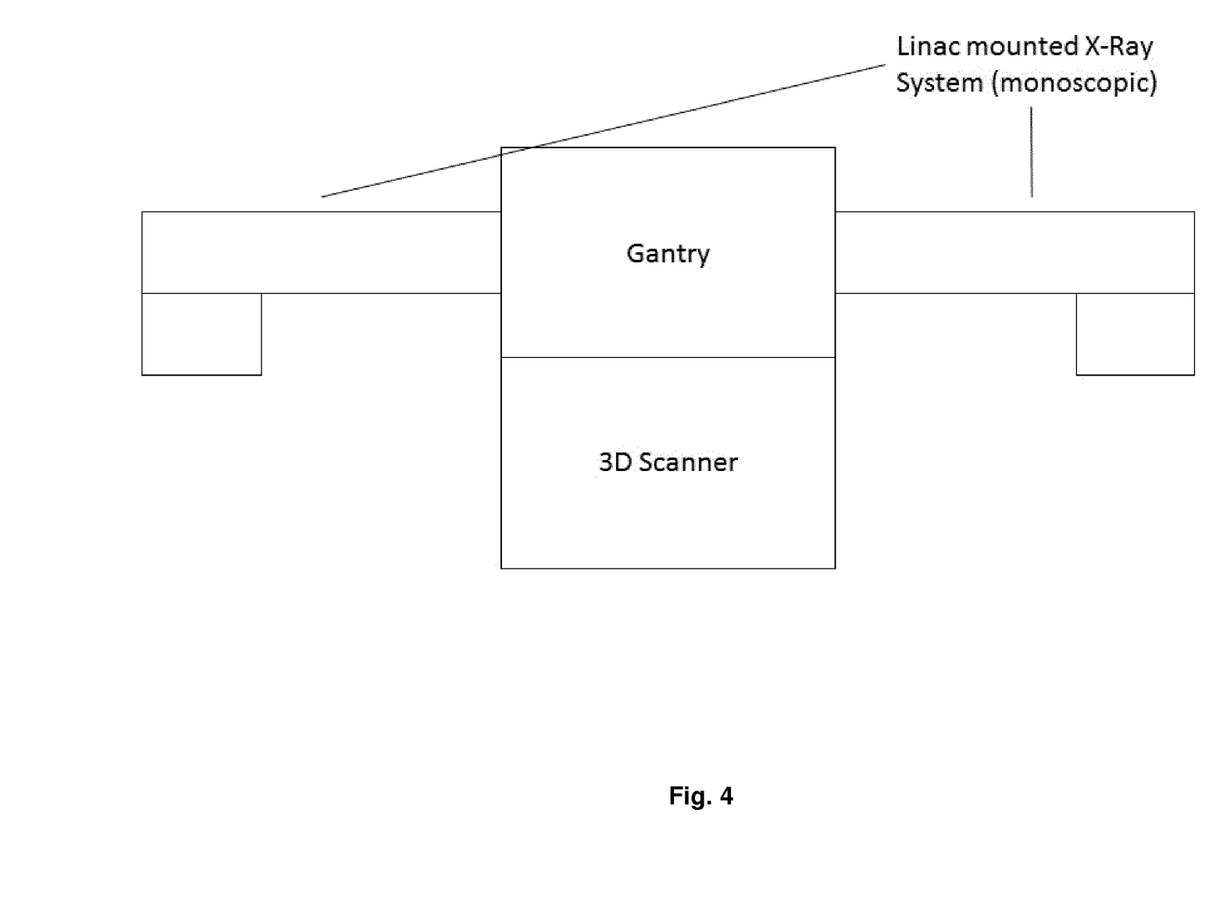

FIG. 4 shows a second example of the system according to the fifth aspect with a monoscopic medical imaging device embodied by a monoscopic x-ray system. The outer constituents of this example correspond to those of the first example of the system according to the fifth aspect.

The invention claimed is:

1. A computer implemented method for determining a pose of an anatomical body part of a patient's body for planning radiation treatment, comprising:
    acquiring three-dimensional reference image data which describes a reference image of both a reference pose of an internal anatomical reference structure of the anatomical body part and a reference pose of an anatomical reference surface of the anatomical body part;
    acquiring surface tracking data which describes a tracking image of a current pose of the anatomical reference surface of the anatomical body part;
    determining a reference surface pose similarity measure by comparing the reference pose of the anatomical reference surface and the current pose of the anatomical reference surface;
    generating reconstructed image data which describes a reconstructed two-dimensional reference image of the reference pose of the internal anatomical reference structure from the reference image of the three-dimensional reference image data;
    acquiring current reference structure image data which describes a current two-dimensional image of a current pose of the internal anatomical reference structure;
    determining a reference structure pose similarity measure by comparing the reference pose of the internal anatomical reference structure and the current pose of the internal anatomical reference structure;
    determining an optimized pose of the anatomical body part based at least on optimal values of the reference surface pose similarity measure and the reference structure pose similarity measure.

2. The method according to claim 1, wherein the reference structure pose similarity measure and the reference surface pose similarity measure are input into an optimization algorithm for simultaneously minimizing:
    any dissimilarity between the reference pose of the internal anatomical reference structure and the current pose of the internal anatomical reference structure and
    any dissimilarity between the reference pose of the anatomical reference surface and the current pose of the anatomical reference surface.

3. The method according to claim 2, further comprising:
    acquiring planning image data which describes a planned pose of the anatomical body part;
    comparing the optimized pose to the planned pose.

4. The method according to claim 3, further comprising at least one of the following steps:
    determining a control signal for controlling emission of a radiation treatment beam by a radiation treatment apparatus based on the result of the comparison; or
    determining a control signal for controlling the position of a patient support device supporting the anatomical body part based on a result of the comparison.

5. The method according to claim 3, wherein the planning image data and the three-dimensional reference image data are at least partly identical.

6. The method according to claim 1, wherein determining the optimized pose comprises changing the reference pose of the internal anatomical reference structure.

7. The method according to claim 1, wherein the surface tracking data has been generated by applying a structured light tracking modality or three-dimensional thermal tracking modality or a combination of structured light and thermal tracking modality or surface scan laser tracking modality or visible digital photography tracking modality or a time-of-flight tracking modality to the anatomical body part.

8. The method according to claim 1, wherein the reconstructed image data and the current reference structure image data describe images of the same imaging modality.

9. The method according to claim 1, wherein the reconstructed image data and the current reference structure image data describe images of different imaging modalities, and wherein the method further comprises a step of acquiring atlas data describing a multimodal atlas of the anatomical body part, wherein the reference structure pose similarity measure is determined based on the atlas data.

10. The method according to claim 9, wherein at least one of the current reference structure image data and the reconstructed image data is transformed into a common imaging modality, wherein the reference structure pose similarity data is determined based on the transformed at least one of the current reference structure image data and the reconstructed image data.

11. The method according to claim 1, wherein the reference surface pose similarity measure is determined by determining an average deviation of surface points or a correspondence of topological equivalents or an image fusion, between the reference image and the tracking image.

12. A non-transitory computer program medium comprising instructions, which, when running on at least one processor of at least one computer, causes the at least one processor to perform the steps of:

acquiring three-dimensional reference image data which describes a reference image of both a reference pose of an internal anatomical reference structure of an anatomical body part and a reference pose of an anatomical reference surface of the anatomical body part;

acquiring surface tracking data which describes a tracking image of a current pose of the anatomical reference surface of the anatomical body part;

determining a reference surface pose similarity measure by comparing the reference pose of the anatomical reference surface and the current pose of the anatomical reference surface;

generating reconstructed image data which describes a reconstructed two-dimensional reference image of the reference pose of the internal anatomical reference structure from the reference image of the three-dimensional reference image data;

acquiring current reference structure image data which describes a current two-dimensional image of a current pose of the internal anatomical reference structure;

determining a reference structure pose similarity measure by comparing the reference pose of the internal anatomical reference structure and the current pose of the internal anatomical reference structure;

determining an optimized pose of the anatomical body part based at least on optimal values of the reference surface pose similarity measure and the reference structure pose similarity measure.

13. A system for determining a deviation between a planned and a current pose between an anatomical body part and a treatment beam source, the system comprising:

one or more processors and memory operably coupled with the one or more processors, wherein the memory stores instructions that, in response to execution of the instructions by the one or more processors, cause the one or more processors to perform the following operations:

acquiring three-dimensional reference image data which describes a reference image of both a reference pose of an internal anatomical reference structure of the anatomical body part and a reference pose of an anatomical reference surface of the anatomical body part;

acquiring surface tracking data which describes a tracking image of a current pose of the anatomical reference surface of the anatomical body part;

determining a reference surface pose similarity measure by comparing the reference pose of the anatomical reference surface and the current pose of the anatomical reference surface;

generating reconstructed image data which describes a reconstructed two-dimensional reference image of the reference pose of the internal anatomical reference structure from the reference image of the three-dimensional reference image data;

acquiring current reference structure image data which describes a current two-dimensional image of a current pose of the internal anatomical reference structure;

determining a reference structure pose similarity measure by comparing the reference pose of the internal anatomical reference structure and the current pose of the internal anatomical reference structure;

determining an optimized pose of the anatomical body part based at least on optimal values of the reference surface pose similarity measure and the reference structure pose similarity measure;

at least one electronic data storage device storing at least the three-dimensional reference image data and planning image data which describes a planned pose of the anatomical body part relative to the treatment beam source;

a medical imaging device for generating the current reference structure image data, an optical tracking device for generating the surface tracking data, wherein the medical imaging device and the optical tracking device are operably coupled to at least one processor of the one or more processors; and a radiation treatment apparatus having the treatment beam source and a patient support unit, wherein the at least one processor is operably coupled to the at least one electronic data storage device for acquiring, from the at least one electronic data storage device, at least the three-dimensional reference image data and the planning image data, and for issuing a control signal to the radiation treatment apparatus for controlling at least one of the functionality of the treatment beam source or the position of the patient support unit on the basis of the result of comparing the planned pose with the optimized pose.

* * * * *